(12) United States Patent
Chiou et al.

(10) Patent No.: US 9,034,833 B1
(45) Date of Patent: May 19, 2015

(54) ANTI-AGING COMPOSITION CONTAINING HIGH LEVELS OF A JASMONIC ACID DERIVATIVE

(71) Applicant: L'OREAL, Paris (FR)

(72) Inventors: Catherine Chiou, Saddle Brook, NJ (US); Lauren E. Manning, Hoboken, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/136,471

(22) Filed: Dec. 20, 2013

(51) Int. Cl.
| | | |
|---|---|---|
| *A61K 31/70* | (2006.01) | |
| *A61K 8/891* | (2006.01) | |
| *A61K 8/37* | (2006.01) | |
| *A61K 8/89* | (2006.01) | |
| *A61Q 19/08* | (2006.01) | |

(52) U.S. Cl.
CPC . *A61K 8/891* (2013.01); *A61K 8/37* (2013.01); *A61K 8/89* (2013.01); *A61Q 19/08* (2013.01)

(58) Field of Classification Search
USPC .......................................................... 514/25
See application file for complete search history.

(56) References Cited

U.S. PATENT DOCUMENTS

| | | | |
|---|---|---|---|
| 4,268,499 A | 5/1981 | Keil | |
| 4,917,882 A | 4/1990 | Strobridge | |
| 5,601,811 A | 2/1997 | Gallagher et al. | |
| 6,524,598 B2 | 2/2003 | Sunkel et al. | |
| 6,696,049 B2 | 2/2004 | Vatter et al. | |
| 7,262,217 B2 | 8/2007 | Baranger et al. | |
| 8,216,555 B2 | 7/2012 | Nieuwenhuijsen | |
| 8,299,127 B2 | 10/2012 | Anjing et al. | |
| 8,461,206 B2 | 6/2013 | Dalko | |
| 8,481,594 B2 | 7/2013 | Boulle et al. | |
| 8,603,502 B2 | 12/2013 | Boulle et al. | |
| 8,609,117 B2 | 12/2013 | Boulle et al. | |
| 8,865,660 B2 * | 10/2014 | Broady ........................... 514/25 | |
| 2003/0064046 A1 | 4/2003 | Omura et al. | |
| 2007/0128137 A1 | 6/2007 | Yoshimi et al. | |
| 2007/0264210 A1 | 11/2007 | Robinson | |
| 2009/0035236 A1 | 2/2009 | Maes et al. | |
| 2010/0168041 A1 * | 7/2010 | Laboureau et al. ............. 514/23 | |
| 2010/0179222 A1 | 7/2010 | Boulle et al. | |
| 2010/0310617 A1 | 12/2010 | Zhang et al. | |
| 2011/0256077 A1 | 10/2011 | Hayakawa | |
| 2012/0088836 A1 | 4/2012 | Dalko | |
| 2012/0322876 A1 | 12/2012 | Kermorvan et al. | |
| 2013/0142740 A1 | 6/2013 | Cziryak et al. | |
| 2013/0345317 A1 | 12/2013 | Chiou | |

FOREIGN PATENT DOCUMENTS

| | | | |
|---|---|---|---|
| CN | 1793822 A | 6/2006 | |
| EP | 1027883 A2 | 8/2000 | |
| EP | 1671680 A1 | 6/2006 | |
| EP | 1990372 A2 | 11/2008 | |
| FR | 2847469 A1 | 5/2004 | |
| FR | 2847470 A1 | 5/2004 | |
| FR | 2909552 A1 | 6/2008 | |
| FR | 2921254 A1 | 3/2009 | |
| FR | 2921255 A1 | 3/2009 | |
| FR | 2940053 A1 | 6/2010 | |
| FR | 2951375 A1 | 4/2011 | |
| FR | 2953718 A1 | 6/2011 | |
| FR | 2954122 A1 | 6/2011 | |
| FR | 2964865 A1 | 3/2012 | |
| FR | 2973693 A1 | 10/2012 | |
| FR | 2977478 A1 | 1/2013 | |
| FR | 2988291 A1 | 9/2013 | |
| FR | 2988292 A1 | 9/2013 | |
| JP | 2001205061 A | 7/2001 | |
| WO | 0069423 A1 | 11/2000 | |
| WO | 2010000584 A2 | 1/2010 | |
| WO | 2011054600 A1 | 5/2011 | |
| WO | 2012084699 A2 | 6/2012 | |
| WO | 2012084701 A2 | 6/2012 | |
| WO | 2012136564 A2 | 10/2012 | |
| WO | 2012136818 A2 | 10/2012 | |

(Continued)

OTHER PUBLICATIONS

C. Tran, J.F. Michelet, L. Simonetti, F. Fiat, A. Garrigues, A. Potter, E. Segot, R.E.B. Watson, C.E.M. Griffiths, O. De Lacharriere, In vitro and in vivo studies with tetra-hyrdo-jasmonic acid (LR2412) reveal its potential to correct signs of skin ageing, Journal of the European Academy of Dermatology and Venereology 2013 European Academy of Dermatology and Venereology, p. 1-9, DOI: 10.1111/jdv.12113.

M. Vonka, J. Kosek, Modelling the morphology evolution of polymer materials undergoing phase separation, Chemical Engineering Journal, 2012, p. 1-11, http://dx.doi.org/10.1016/j.cej.2012.06.091.

U.S. Appl. No. 14/136,471, filed Dec. 20, 2013, Chiou.
U.S. Appl. No. 14/136,562, filed Dec. 20, 2013, Galdi.
U.S. Appl. No. 14/136,634, filed Dec. 20, 2013, Chiou.

(Continued)

*Primary Examiner* — Rei-Tsang Shiao
(74) *Attorney, Agent, or Firm* — McNees, Wallace & Nurick LLC

(57) ABSTRACT

A water-releasing anti-aging composition in the form of an emulsion and process for preparing the anti-aging composition are provided. The anti-aging composition includes an aqueous phase and an oil phase. The aqueous phase includes at least one electrolytic jasmonic acid derivative at a concentration by weight of about 2% to about 20%, based upon weight of the composition. The oil phase includes dimethicone at a concentration by weight of about 1% to about 25%, and an emulsifying crosslinked siloxane elastomer at a concentration by weight of about 0.1% to about 20%, both based upon weight of the composition. The anti-aging composition has a phase ratio of the aqueous phase to the oil phase of about 3.0 to about 12.0. The anti-aging composition converts from an emulsion to a plurality of droplets upon application of shear.

19 Claims, No Drawings

(56) References Cited

FOREIGN PATENT DOCUMENTS

| WO | 2012143645 | A2 | 10/2012 |
| WO | 2013007637 | A2 | 1/2013 |
| WO | 2013007647 | A1 | 1/2013 |
| WO | PCT/US2013/045613 | | 6/2013 |

OTHER PUBLICATIONS

U.S. Appl. No. 14/136,714, filed Dec. 20, 2013, Chiou.
U.S. Appl. No. 13/529,059, filed Jun. 21, 2012, Abandoned, Chiou.
U.S. Appl. No. 13/855,495, filed Apr. 2, 2013, Chiou.

\* cited by examiner

ANTI-AGING COMPOSITION CONTAINING HIGH LEVELS OF A JASMONIC ACID DERIVATIVE

FIELD OF THE INVENTION

The present invention is directed to anti-aging compositions and methods of using anti-aging compositions. More specifically, the present invention is directed to an anti-aging composition in the form of an emulsion having an aqueous phase including at least one jasmonic acid derivative and an oil phase containing dimethicone and an emulsifying crosslinked siloxane elastomer. The anti-aging composition is capable of carrying high amounts of jasmonic acid derivatives in a texturally pleasing manner, without experiencing separation of the emulsion. The present invention also provides a water-releasing effect when applied onto a keratinous substrate such as skin, hair or nails. The water-releasing effect enables the composition, initially in the form of an emulsion, to be converted into a plurality of droplets upon application of shear such as, for example, rubbing.

BACKGROUND OF THE INVENTION

Jasmonic acid derivatives have been shown to be an effective anti-aging active as is evidenced in US2010/0179222, the entire content of which is hereby incorporated by reference. A particularly effective example thereof is sodium tetrahydrojasmonate. Its anti-aging/anti-wrinkle efficacy has been well demonstrated. However, due to its high electrolyte content and amphiphilic characteristics (i.e. possessing both hydrophilic and lipophilic properties), sodium tetrahydrojasmonate is not easily formulated into an emulsion having desirable texture and, more importantly, stability profiles.

Therefore, it is an object of the present invention to provide an anti-aging composition in the form of a stable emulsion capable of carrying large quantities of jasmonic acid derivatives, which is also tactilely pleasing to consumers upon application.

BRIEF DESCRIPTION OF THE INVENTION

All numbers expressing quantities of ingredients and/or reaction conditions are understood as being modified in all instances by the term "about", unless otherwise stated.

In an exemplary embodiment, an anti-aging composition in the form of a stable, tactilely pleasing emulsion is provided. The composition includes an aqueous phase and an oil phase. The aqueous phase contains at least one jasmonic acid derivative at a concentration of from about 2% to about 20% by weight, based upon the total weight of the composition. The oil phase contains dimethicone at a concentration by weight of from about 1% to about 25%, based upon the total weight of the composition, and an emulsifying crosslinked siloxane elastomer at a concentration by weight of from about 0.1% to about 20%, based upon the total weight of the composition. The anti-aging skin care composition has a phase ratio of aqueous phase to oil phase of from about 3 to about 12. The anti-aging composition converts from an emulsion to a plurality of droplets upon application of force such as, for example, rubbing with one's fingers or using an electromechanical force-imparting device such as, for example, an electromechanical cleansing brush.

In another exemplary embodiment, a method of diminishing signs of aging on keratinous substrates is provided. The method includes applying the above-disclosed anti-aging composition onto the surface of a keratinous substrate, followed by application of force onto the composition present on the keratinous substrate.

Other features and advantages of the present invention will be apparent from the following more detailed description of the preferred embodiment which illustrates, by way of example, the principles of the invention.

DETAILED DESCRIPTION OF THE INVENTION

"Keratinous substrate", as used herein, includes but is not limited to skin, hair, and nails.

"Force", as used herein, includes shear/friction produced by a rubbing motion of an end user's fingers, an electromechanical cleansing device having a movable brush with bristles, and/or an electromechanical device that produces a tapping motion, similar to one's fingers tapping on the surface of the skin.

"Homogenous" means substantially uniform throughout, i.e., a single phase mixture.

In the present application the term "ambient temperature" means a temperature of about 25° C.

In the present application the term "water releasing", as used herein, describes the phenomenon wherein, after application of an anti-aging composition onto a target substrate, force is then applied onto the composition causing the water-in-oil type emulsion to rupture, which in turn causes the internal aqueous phase containing the jasmonic acid derivative(s) to emerge in the form of droplets.

The anti-aging composition and method of the present invention can comprise, consist of, or consist essentially of the essential elements and limitations of the invention described herein, as well as any additional or optional ingredients, components, or limitations described herein or otherwise useful in compositions intended for topical application onto keratinous substrates.

It has been surprisingly discovered by the inventors that high concentrations of jasmonic acid derivatives such as, for example, sodium tetrahydrojasmonate, can be formulated into a stable water-in-oil type emulsion which, though initially in the form of a cream, possesses a transformative water-releasing effect upon application of force such as, for example, shear. The transformative water-releasing effect is that the cream transforms into droplets containing the aqueous phase with the jasmonic acid derivative when exposed to force such as the shearing effect caused by rubbing/massaging the emulsion present on the surface of the keratinous substrate, thereby forcing the jasmonic acid derivative-containing droplets into the keratinous substrate.

One advantage of an embodiment of the present disclosure includes providing a stable anti-aging composition capable of carrying relatively high levels of electrolytic jasmonic acid derivatives without undergoing phase separation, i.e. breaking the emulsion. Yet another advantage of an embodiment of the present disclosure is providing an anti-aging composition capable of producing a water-releasing effect onto a keratinous substrate, such as skin. The water-releasing effect enables the composition, initially in the form of an emulsion, to be converted into a plurality of droplets carrying high levels of electrolytic jasmonic acid derivatives upon application of force such as, for example, shear caused by an end user's rubbing of the composition onto the surface of a target keratinous substrate. The droplets, in turn, enable the jasmonic acid derivatives present in said droplets to effectively penetrate into a target keratinous substrate.

The water-in-oil emulsion system of the present invention typically has a white, glossy cream appearance. However, it may be modified so as to have a transparent gel-like or matte appearance by adjusting its refractive index. When the anti-aging composition is deposited onto a target keratinous substrate, followed by application of force, the composition quickly releases the aqueous phase containing the jasmonic acid derivatives in the form of bead like droplets, thereby enabling the jasmonic acid derivatives present in the aqueous phase to be forced into the surface of the target keratinous substrate.

Aqueous Phase

The aqueous phase present in the anti-aging composition according to the disclosure includes at least one jasmonic acid derivative, water, and other aqueous phase ingredients. The aqueous phase of the anti-aging composition is at a concentration, by weight, of from about 60% to about 92%, or alternatively from about 70% to about 90%, or alternatively from about 80% to about 90% based upon weight of the anti-aging composition.

Electrolytic Anti-Aging Ingredient

The aqueous phase present in the anti-aging composition according to the disclosure includes at least one electrolytic jasmonic acid derivative at a concentration, by weight, of from about 2% to about 20%, or alternatively from about 4% to about 15%, or alternatively from about 4% to about 10% based upon weight of the composition.

Suitable examples of electrolytic jasmonic acid derivatives include those corresponding to the following formula (I):

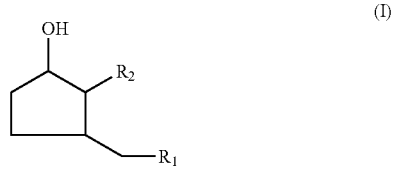

(I)

in which:

$R_1$ represents a COORS radical, $R_3$ denoting a hydrogen atom or a $C_1$-$C_4$ alkyl radical, optionally substituted by one or more hydroxyl groups;

$R_2$ represents a saturated or unsaturated and linear hydrocarbon radical containing from 1 to 18 carbon atoms or a saturated or unsaturated and branched or cyclic hydrocarbon radical containing from 3 to 18 carbon atoms;

and also the optical isomers thereof, and corresponding salts.

Preferably, $R_1$ denotes a radical chosen from —COOH, COOMe, —COO—$CH_2$—$CH_3$, —COO—$CH_2$—CH(OH)—$CH_2$OH, —COO$CH_2$—$CH_2$—$CH_2$OH or —COO$CH_2$—CH(OH)—$CH_3$. Preferentially, $R_1$ denotes a —COOH radical.

Preferentially, $R_2$ denotes a saturated or unsaturated and linear hydrocarbon radical preferably containing from 2 to 7 carbon atoms. In particular, $R_2$ may be a pentyl, pentenyl, hexyl or heptyl radical.

According to one embodiment, the compound of formula (I) is chosen from 3-hydroxy-2-[(2Z)-2-pentenyl]cyclopentaneacetic acid or 3-hydroxy-2-pentylcyclopentaneacetic acid. Preferably, compound (I) is 3-hydroxy-2-pentylcyclopentaneacetic acid; this compound may especially be in the form of the sodium salt.

The salts of the compounds that may be used according to the invention are chosen in particular from salts of alkali metals, for example sodium or potassium; salts of alkaline-earth metals, for example calcium, magnesium or strontium; metal salts, for example zinc, aluminium, manganese or copper; salts of ammonium of formula $NH_4^+$; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts. Salts chosen from sodium, potassium, magnesium, strontium, copper, manganese or zinc salts are preferably used. The sodium salt is preferentially used.

In one embodiment, a particularly preferred electrolytic jasmonic acid derivative is sodium tetrahydrojasmonate.

The salt content of the electrolytic jasmonic acid derivatives will typically range from about 3% to about 70%, or alternatively from about 8% to about 50%, or alternatively from about 9% to about 15%, based upon the weight of the jasmonic acid derivative.

Water

The aqueous phase present in the anti-aging composition according to the disclosure includes water at a concentration by weight of about 60% to about 92%, or alternatively about 70% to about 90% or alternatively about 80% to about 90%, based upon the total weight of the composition. The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such zinc, copper, magnesium, etc., reconstituting the characteristics of thermal water.

Oil Phase

The oil phase present in the anti-aging composition according to the disclosure includes dimethicone and an emulsifying crosslinked siloxane elastomer. The oil phase of the water-releasing anti-aging composition is at a concentration by weight of about 8% to about 25%, or alternatively about 10% to about 20%, or alternatively about 10% to about 15%, based upon the total weight of the anti-aging composition.

Dimethicone

The oil phase present in the anti-aging composition according to the disclosure includes dimethicone at a concentration, by weight, of about 1% to about 25%, or alternatively about 2% to about 20%, or alternatively about 4% to about 15%, based upon weight of the composition.

Emulsifying Crosslinked Siloxane Elastomer

The oil phase present in the anti-aging composition according to the disclosure includes an emulsifying crosslinked siloxane elastomer at a concentration, by weight, of about 0.1% to about 20%, or alternatively about 0.3% to about 10%, or alternatively about 0.5% to about 7%, based upon weight of the composition.

Examples of suitable emulsifying crosslinked siloxane elastomers, include, but are not limited to, substituted or unsubstituted dimethicone/copolyol crosspolymer, dimethicone and dimethicone/PEG-10/15 crosspolymers, substituted or unsubstituted dimethicone/polyglyceryl crosspolymer, dimethicone and dimethicone/polyglycerin-3 crosspolymer. Such suitable emulsifying crosslinked siloxane elastomers are sold or made, for example, under the names of "KSG-210" a polyether-modified crosspolymer with an INCI name of dimethicone (and) dimethicone/PEG-10/15 crosspolymer, and "KSG-710" a polyglycerin-modified crosspolymer with an INCI name of dimethicone (and) dimethicone/polyglycerin-3 crosspolymer, both available from Shin-Etsu Silicones of America, Inc. (Akron, Ohio).

Co-Emulsifier

The oil phase present in the anti-aging composition according to the disclosure may optionally include a co-emulsifier at a concentration by weight of about 0.01% to about 1%, or alternatively about 0.05% to about 0.9%, or alternatively about 0.07% to about 0.8%, based upon the total weight of the composition. If the co-emulsifier concentration exceeds 1% by weight of the anti-aging composition, then the anti-aging composition may still form an emulsion but the desirable transformative effect of cream changing to droplets upon application of shear is not achieved.

Suitable examples of co-emulsifiers include polyether substituted linear or branched polysiloxane copolymers. One preferred co emulsifier is PEG-10 dimethicone available under the tradename of ES-5612 from Dow Corning Corporation (Midland, Mich.), or KF-6017 from Shin-Etsu (Akron, Ohio). Another preferred co-emulsifier is dimethicone (and) PEG/PPG-18/18 dimethicone available under the tradename of ES-5226 DM from Dow Corning Corporation (Midland, Mich.). Other suitable co emulsifiers include, PEG-9 polydimethylsiloxyethyl dimethicone available under the tradename KF-6028 and PEG-9, lauryl PEG-9 polydimethylsiloxyethyl dimethicone available under the tradename KF-6038, both available from Shin-Etsu (Akron, Ohio). Another suitable example of a co-emulsifier is polyoxyalkylene copolymers also known as silicone polyethers. Polyoxyalkylene copolymers are described in detail in U.S. Pat. No. 4,268,499, which is incorporated herein by reference in its entirety. A particularly preferred polyoxyalkylene copolymer is known by its CTFA designation as dimethicone copolyol. A particularly preferred form of dimethicone copolyol is supplied by Dow Corning as DC5225C.

Optional Powders

The anti-aging composition of the present disclosure may optionally include powders. The optional powders provide formulas that are smoother and softer on the skin. Representative powders include, but are not limited to talc, mica, magnesium carbonate, calcium carbonate, magnesium silicate, aluminum magnesium silicate, silica, titanium dioxide, zinc oxide, red iron oxide, yellow iron oxide, black iron oxide, polyethylene powder, methacrylate powder, polystyrene powder, silk powder, crystalline cellulose, starch, titanated mica, iron oxide titanated mica, bismuth oxychloride, and the like. Additional powders include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide. A representative powder includes, for example, polymethylsilsesquioxane. Powders may be present in the compositions in amounts generally ranging from about 0.1% to about 10% by weight, based on the total weight of the composition.

Phase Ratio

The phase ratio is calculated by dividing the total weight of the aqueous phase by the total weight of the oil phase. The anti-aging composition of the present disclosure as a water-in-oil emulsion has a ratio by weight of the aqueous phase to oil phase of from about 3 to about 12, or alternatively about 4 to about 10, or alternatively about 5 to about 9. The phase ratio excludes any additional optional powders that may be added to the composition. Without intending to be bound by theory, this phase ratio is believed to be critical to (1) the stability of the emulsion in view of the high concentration of jasmonic acid derivative(s) contained therein, and (2) the formation of droplets upon application of force onto the emulsion.

Water-Releasing Effect

With respect to the present invention, a good water-releasing effect of the water-in-oil emulsion means that the water-releasing effect has an evaluation result of more than or equal to a score of 3 in the evaluation system described below. The test method and evaluation score of the test system are described below.

About 0.2 g of a water-in-oil emulsion sample of cosmetic composition is taken and placed on the back of a hand, then it is applied thereon by circling gently with the middle finger and ring finger of the other hand, and then the phenomenon of the water-releasing effect is observed when the circling application reaches 20 cycles, and evaluated by a 5-level scoring system. A score of 5 represents that more than 10 bead-like water drops having an average diameter of more than or equal to 3 mm appear, or more than 20 bead-like water drops having an average diameter of more than or equal to 1 mm appear. A score of 4 represents that 2-10 bead-like water drops having an average diameter of more than or equal to 3 mm appear, or 10-20 bead-like water drops having an average diameter of more than or equal to 1 mm appear and the bead-like water drops having an average of more than or equal to 3 mm are no more than 10. A score of 3 represents that 2-9 bead-like water drops having an average diameter of more than or equal to 1 mm appear and there is at most 1 bead-like water drop having an average diameter of more than or equal to 3 mm, or 10-20 head-like water drops having an average diameter of 1 mm appear. A score of 2 represents that 2-9 bead-like water drops having an average diameter of 1 mm appear. A score of 1 represents that no water drop appears. Each level between scores 5 to 4, 4 to 3, 3 to 2, and 2 to 1 shows that the water-releasing effect is between the two end values described above, and the lower the score, the poorer the water-releasing effect.

In one embodiment, the water-releasing effect of the cosmetic composition of the present disclosure is about 3 to 5.

EXAMPLES

TABLE 1

| | Inventive Examples | | | |
|---|---|---|---|---|
| Phase | INCI Name | Ex. 1 | Ex. 2 | Ex. 3 |
| A | DIMETHICONE/PEG-10/15 CROSSPOLYMER | 1.25 | 1.25 | 1.25 |
| A | PEG-10 DIMETHICONE | 0.1 | 0.1 | 0.1 |
| A | DIMETHICONE | 10.7 | 10.7 | 10.7 |
| B | WATER, PRESERVATIVES | QS 100 | QS 100 | QS 100 |
| B | SODIUM TETRAHYDROJASMONATE | 4 | 7 | 15 |

TABLE 1-continued

Inventive Examples

| Phase | INCI Name | Ex. 1 | Ex. 2 | Ex. 3 |
|---|---|---|---|---|
| B | GLYCERIN | 18 | 18 | 0 |
| B | DIRPOPYLENE GLYCOL | 2.7 | 4.4 | 9.4 |
| B | PROPANEDIOL | 5 | 5 | 0 |
| B | DISODIUM EDTA | 0.1 | 0.1 | 0 |
| B | Botanical Extracts | 0.05 | 0.05 | 0 |
| B | NIACINAMIDE | 5 | 5 | 0 |
| C | POLYMETHYLSILSESQUIOXANE | 1 | 1 | 1 |
|  | Total (%) | 100 | 100 | 100 |
|  | Brookfield Viscosity (cp or mPa.s) | 25,000 | 18,000 | 21,000 |
|  | Total Oil Phase (%) | 12.1 | 12.1 | 12.1 |
|  | Total Water Phase (%) | 87.0 | 87.0 | 87.0 |
|  | Ratio (water phase/oil phase)* | 7.2 | 7.2 | 7.2 |
|  | Water Releasing Effect (scale of 1 to 5) | 3 | 3 to 4 | 4 |
|  | Texture/Appearance: | Translucent to opaque cream-gel, water droplets released upon. rubbing. | | |

*Excludes powder (Phase C)

In making each of the examples in Table 1, the following procedure is used.

The ingredients of Phase B (aqueous) are mixed together in a side beaker with a rotor/stator mixer until all solids are dissolved, giving a clear solution. If needed, Phase B (aqueous) can be gently heated to about 40-45° C. until all solids are dissolved. The ingredients of Phase A (oil phase) are placed in a main beaker and are mixed well with a propeller mixer at about 600-700 RPM and set aside. The mixture of aqueous phase ingredients (Phase B) are slowly added to the mixed ingredients of Phase A (oil phase) using a propeller mixer over a period of 10-15 minutes for an about 1 kg batch. As the viscosity of the mixture increases, the stirring speed is increased from 700 rpm to about 1200 rpm. As the aqueous phase is mixed into the oil phase a water-in-oil emulsion is formed. Optionally, powders are added to the batch and are mixed into the water-in-oil emulsion.

Example 1

Inventive

The water-in-oil emulsion of inventive Example 1 is prepared according to the procedure outlined above. Example 1 includes 4% sodium tetrahydrojasmonate. The total weight percentage of the aqueous or water phase is about 87.0 and the total weight percent of the oil phase is about 12.1, making the a ratio of the aqueous phase to oil phase about 7.2. The emulsion formed in Example 1 is a translucent to opaque cream-gel that releases droplets upon rubbing. The water/silicone emulsion boundary layer is stable and includes droplets having various droplet sizes, with some droplets as large as 50 microns or greater. The viscosity of Example 1 is measured using a Brookfield Viscometer, using spindle T-D and speed set at 10 rpm for 1 minute. The viscosity of Example 1 is about 25,000 cp (mPa·s). The water-releasing effect of Example 1 is measured by placing about 0.2 g of the cosmetic composition on the back of a hand, then applying thereon by circling gently with the middle finger and ring finger of the other hand. The phenomenon of the water-releasing effect is observed when the circling application reaches 20 cycles. Approximately 15-20 bead-like droplets having an average diameter of 1 mm appear. The water-releasing effect of the water-in-oil emulsion of Example 1 is about 3.

Example 2

Inventive

The water-in-oil emulsion of inventive Example 2 is prepared according to the procedure outlined above. Example 2 includes 7% sodium tetrahydrojasmonate. The total weight percentage of the aqueous or water phase is about 87.0 and the total weight percent of the oil phase is about 12.1, making the a ratio of the aqueous phase to oil phase about 7.2. The emulsion formed in Example 2 is a translucent to opaque cream-gel that releases droplets upon rubbing. The water/silicone emulsion boundary layer is stable and includes droplets having various droplet sizes, with some droplets as large as 50 microns or greater. The viscosity of Example 2 is measured using a Brookfield Viscometer, using spindle T-D and speed set at 10 rpm for 1 minute. The viscosity of Example 2 is about 18,000 cp (mPa·s). The water-releasing effect of Example 2 is measured by placing about 0.2 g of the cosmetic composition on the back of a hand, then applying thereon by circling gently with the middle finger and ring finger of the other hand. The phenomenon of the water-releasing effect is observed when the circling application reaches 20 cycles. Approximately 1-5 bead-like droplets of more than or equal to 3 mm appears and approximately 15-18 bead-like droplets having an average diameter of more than or equal to 1 mm appear. The water-releasing effect of the water-in-oil emulsion of Example 2 is about 3 to 4.

Example 3

Inventive

The water-in-oil emulsion of inventive Example 3 is prepared according to the procedure outlined above. Example 3 includes 15% sodium tetrahydrojasmonate. The total weight percentage of the aqueous or water phase is about 87.0 and the total weight percent of the oil phase is about 12.1, making the a ratio of the aqueous phase to oil phase about 7.2. The emulsion formed in Example 3 is a translucent to opaque cream-gel that releases droplets upon rubbing. The water/silicone emulsion boundary layer is stable and includes droplets having various droplet sizes, with some droplets as large as 50 microns or greater. The viscosity of Example 3 is measured using a Brookfield Viscometer, using spindle T-D and speed set at 10 rpm for 1 minute. The viscosity of Example 3 is about 21,000 cp (mPa·s). The water-releasing effect of Example 3 is measured by placing about 0.2 g of the cosmetic composition on the back of a hand, then applying thereon by circling gently with the middle finger and ring finger of the other hand. The phenomenon of the water-releasing effect is observed when the circling application reaches 20 cycles. Approximately 5-9 bead-like droplets of more than or equal to 3 mm appears and approximately 15-18 bead-like droplets having an average diameter of more than or equal to 1 mm appear. The water-releasing effect of the water-in-oil emulsion of Example 3 is about 4.

TABLE 2

Example 4 (Comparative)

| Phase | INCI Name | Ex. 4 |
|---|---|---|
| A | WATER | 56.85 |
| A | GLYCERIN | 7 |
| A | DIRPOPYLENE GLYCOL | 2.7 |
| A | SODIUM TETRAHYDROJASMONATE | 4 |
| A | PHENOXYETHANOL | 0.7 |
| A | NIACINAMIDE | 5 |
| A | METHYLPARABEN | 0.3 |
| B | DIMETHICONE | 5 |
| B | BUTYROSPERMUM PARKII (SHEA) BUTTER | 2 |
| B | ISONONYL ISONONANOATE | 1.5 |
| B | PENTAERYTHRITYL TETRAETHYLHEXANOATE | 3 |
| B | BEESWAX | 1 |
| B | GLYCOL DISTEARATE | 1 |
| B | GLYCERYL STEARATE (and) PEG-100 STEARATE | 1.6 |
| B | DIMETHICONE (and) DIMETHICONOL | 2 |
| B | CETEARYL ALCOHOL (and) CETEARYL GLUCOSIDE | 5 |
| B | ARACHIDYL ALCOHOL (and) BEHENYL ALCOHOL (and) ARACHIDYL GLUCOSIDE | 2 |
| C | XANTHAN GUM | 0.3 |
| D | Botanical Extract | 0.05 |
| E | POLYMETHYLSILSESQUIOXANE | 1 |
| E | NYLON-12 | 1 |
| | Total (%) | 100 |
| | Brookfield Viscosity (cp or mPa·s): 24 hours | 18,000 |
| | Brookfield Viscosity (cp or mPa·s): 1 month | 86,000 |
| | Water Releasing Effect (scale of 1 to 5) | 1 |
| | Texture/Appearance: Glossy, white cream, very stringy, texture thickened over time, no water-droplet releasing effect | |

The comparative Example 4 was prepared by heating water phase and oil phase separately to 80° C. The oil phase was added to the water phase while mixing until homogeneous. The resulted emulsion was cooled to about room temperature, followed by adding xanthan gum and botanical extract. Optionally, powders were added and mixed well.

The oil-in-water emulsion of Example 4 is a typical emulsion commonly seen in the skin care preparations. Example 4 includes about 4% by weight sodium tetrahydrojasmonate. The emulsion formed in Example 4 is a glossy, white cream that does not release droplets upon rubbing. The viscosity of Example 4 is measured using a Brookfield Viscometer, using spindle T-D and speed set at 10 rpm. The viscosity of Example 4 is 18,000 cp (mPa·s) at 24 hours after manufactured. The texture of Example 4 is very stringy upon pick-up by finger tips. The viscosity of Example 4 increases to 86,000 cp (mPa·s) after 1 month at ambient conditions, resulting in an undesirable stability issue. The water-releasing effect of Example 4 is measured by placing about 0.2 g of the cosmetic composition on the back of a hand. The cosmetic composition is applied thereon by circling gently with the middle finger and ring finger of the other hand. The phenomenon of the water-releasing effect is observed when the circling application reaches 20 cycles. No bead-like droplets having an average diameter of more than or equal to 1 mm appeared. The water-releasing effect of the water-in-oil emulsion of Example about 1; therefore, Example 4 has no water-releasing effect.

TABLE 3

Example 5 (Comparative)

| Phase | INCI Name | Ex. 5 |
|---|---|---|
| A | WATER | 43.2 |
| A | GLYCERIN | 11 |
| A | DIRPOPYLENE GLYCOL | 2.7 |
| A | DISODIUM EDTA | 0.1 |
| A | NIACINAMIDE | |
| A | ADENOSINE | 0.1 |
| A | Botanical Extracts | 0.1 |
| A | POLYACRYLAMID (and) C13-14 ISOPARAFFIN (and) LAURETH-7 | 2 |
| A1 | SODIUM TETRAHYDROJASMONATE | 4 |
| A2 | POLYACRYLATE CROSSPOLYMER-6 | 5 |
| B | CETYL ALCOHOL | 2.5 |
| B | BEHENYL ALCOHOL | 1.75 |
| B | STEARTC ACID | 1.5 |
| B | CETEARYL ALCOHOL (and) CETEARYL GLUCOSIDE | 0.7 |
| B | POLOXAMER 338 | 0.4 |
| B | PEG-100 STEARATE | 0.25 |
| B | DIMETHICONE | 3 |
| B | PENTAERYTHRITYL TETRAETHYLHEXANOATE | 3 |
| B | ISOPROPYL ISOSTEARATE | 2.6 |
| B | DIMETHICONE | 0.5 |
| B | PHENOXYETHANOL | 0.7 |
| B | CAPRYLYL GLYCOL | 0.2 |
| B | OCTYLDODECANOL | |
| B | CAPRYLOYL SALICYLIC ACID | 0.3 |
| C | DIMETHICONE | 3.6 |
| C | CARBOMER | 0.1 |
| C | SODIUM HYALURONATE | 0.1 |
| D | PTFE | 1 |
| D | POLYETHYLENE | 1 |
| | Total (%) | 100 |
| | Brookfield Viscosity (cp or mPa·s) | 113,000 |
| | Water Releasing Effect (scale of 1 to 5) | 1 |
| | Texture/Appearance: Thick, greasy cream. Very difficult to pick up with finger tips, oil phase separated to the top within days. No water-droplet releasing effect. | |

The comparative Example 5 was prepared by heating water phase and oil phase separately to 80° C. The oil phase was added to the water phase while mixing until homogeneous. The resulting emulsion was cooled to about room temperature, followed by adding xanthan gum and botanical extract. Optionally, powders were added and mixed well.

The oil-in-water emulsion of Example 5 utilizes high concentrations of water phase thickeners, such as polyacrylamide, Polyacrylate Crosspolymer-6 and carbomer. This is a common approach to stabilize active ingredients with high electrolytic properties. Example 5 includes about 4% by weight sodium tetrahydrojasmonate. The emulsion formed in Example 5 is a thick, greasy cream that does not release droplets upon rubbing. The viscosity of Example 5 is measured using a Brookfield Viscometer, using spindle T-D and speed set at 10 rpm. The viscosity of Example 5 is 113,000 cp (mPa·s) at 24 hours after manufactured and has maintained at a steady viscosity range over time. However, the texture of Example is very greasy and is difficult to pick-up by finger tips. Further, a layer of clear oil phase was separated from the emulsion after a month stored at the ambient conditions, rendering an unacceptable stability problem.

The water-releasing effect of Example 5 is measured by placing about 0.2 g of the cosmetic composition on the back of a hand. The cosmetic composition is applied thereon by circling gently with the middle finger and ring finger of the other hand. The phenomenon of the water-releasing effect is observed when the circling application reaches 20 cycles. No bead-like droplets having an average diameter of more than or equal to 1 mm appeared. The water-releasing effect of the water-in-oil emulsion of Example 5 is about 1; therefore, Example 5 has no water-releasing effect.

TABLE 4

Example 6 (Comparative)

| Phase | INCI Name | Ex. 6 |
|---|---|---|
| A | Dimethicone (and) Dimethicone/PEG-10/15 Crosspolymer (76/24) | 4 |
| A | Dimethicone (and) Dimethiconol (88/12) | 1 |
| A | Dimethicone | 6 |
| A | Trisiloxane | 16 |
| B | Water | 59.3 |
| B | Phenoxyethanol | 0.6 |
| B | Caprylyl glycol | 0.2 |
| B | Hexylene glycol | 0.1 |
| B | Iodopropynyl Butylcarbamate (10%) | 0.1 |
| B | Polyaminoprobyl Biguanide (20% in water) | 0.2 |
| B | Butylene glycol | 2 |
| B | Glycerin | 10 |
| B | Sodium Citrate | 0.5 |
| | Total (%) | 100 |
| | Brookfield Viscosity(cp or mPa · s) | 5000 |
| | Total Oil Phase (%) | 27 |
| | Total Water Phase (%) | 73 |
| | Ratio (water phase/oil phase) | 2.7 |
| | Water Releasing Effect (scale of 1 to 5) | 1 |
| | Texture: Translucent, milky serum; watery on skin upon application. No water-droplet releasing effect. | |
| | Microscope: Unstable emulsion with leaking border, indicating potential instability of the emulsion. | |

In making comparative Example 6, the following procedure was used. The ingredients of Phase B (aqueous) are mixed in together in a side breaker using a stirring bar to mix well and dissolve all solids. The ingredients of Phase A (oil phase) are placed in a main beaker and mixed well with a propeller mixer at about 600-700 RPM and set aside. The mixture of aqueous phase ingredients (Phase B) are slowly added to the mixed ingredients of Phase A using a prop mixer over a period of 10-15 minutes for a 1 kg batch. As viscosity slowly increased, the stirring speed is increased from 700 RPM to 1000 RPM to form a serum.

Comparative Example 6, in contrast to the present disclosure, has a total weight percentage of the aqueous phase or water phase of about 73% and a total weight percentage of oil of about 27%, making the ratio of the aqueous phase to oil phase about 2.7. Comparative Example 6 forms a translucent, milky serum that is watery on skin upon application. The viscosity of comparative Example 6 is measured using a Brookfield Viscometer, using spindle T-D and speed set at 10 rpm for 1 minute. The viscosity of comparative Example 6 is about 5,000 cp (mPa·s). The water-releasing effect of comparative Example 6 is measured by placing about 0.2 g of the cosmetic composition on the back of a hand, then applying thereon by circling gently with the middle finger and ring finger of the other hand. No bead-like droplets having an average diameter of more than or equal to 1 mm appeared. The water-releasing effect of the serum of comparative Example 6 is about 1; therefore, comparative Example 6 has no water-releasing effect.

Comparative Example 6 is generally unstable. The microscope shows that the W; Si boundary has a leaking border, indicating potential instability of emulsion. Though the serum of comparative Example 6 initially forms as an emulsion, after 3 days of freeze-thaw cycles, the serum completely separates.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A composition comprising:
    an aqueous phase containing at least one electrolytic jasmonic acid derivative at a concentration by weight of from about 2% to about 20%, based upon weight of the composition, wherein the electrolytic jasmonic acid derivative corresponds to formula (I):

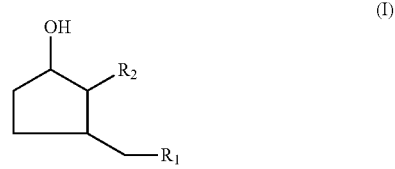

(I)

in which:
    R1 represents a COOR3 radical, R3 denoting a hydrogen atom or a C1-C4 alkyl radical, optionally substituted by one or more hydroxyl groups; and
    R2 represents a saturated or unsaturated and linear hydrocarbon radical containing from 1 to 18 carbon atoms or a saturated or unsaturated and branched or cyclic hydrocarbon radical containing from 3 to 18 carbon atoms; optical isomers; and corresponding salts; and
an oil phase containing:
    dimethicone, at a concentration by weight of from about 1% to about 25, based upon weight of the composition; and
    an emulsifying crosslinked siloxane elastomer at a concentration, by weight, of about 0.1% to about 20%, based upon weight of the composition;
wherein a phase ratio of the aqueous phase to the oil phase is about 3.0 to about 12.0; and
wherein the composition converts from an emulsion to a plurality of droplets upon application of shear.

2. The composition of claim 1, wherein the at least one electrolytic jasmonic acid derivative is sodium tetrahydrojasmonate.

3. The composition of claim 1, wherein the at least one electrolytic jasmonic acid derivative has a salt content of from about 3 to about 70% by weight, based on the weight of the derivative.

4. The composition of claim 1, wherein the emulsifying crosslinked siloxane elastomer comprises a substituted or unsubstituted dimethicone/copolyol crosspolymer.

5. The composition of claim 4, wherein the emulsifying crosslinked siloxane elastomer is dimethicone/PEG-10/15 crosspolymer.

6. The composition of claim 1, wherein the emulsifying crosslinked siloxane elastomer comprises a substituted or unsubstituted dimethicone/polyglyceryl crosspolymer.

7. The composition of claim 6, wherein the emulsifying crosslinked siloxane elastomer is dimethicone/polyglycerin-3 crosspolymer.

8. The composition of claim 1, wherein the oil phase further includes a co-emulsifier.

9. The composition of claim 8, wherein the co-emulsifier is at a concentration, by weight, of about 0.01% to about 1%, based upon weight of the composition.

10. The composition of claim 9, wherein the co-emulsifier is a polyoxyalkylene copolymer.

11. The composition of claim 10, wherein the co-emulsifier is chosen from PEG-10 dimethicone, PEG-9 polydimethylsiloxyethyl dimethicone and PEG-9, lauryl PEG-9 polydimethylsiloxyethyl dimethicone, dimethicone and PEG PPG-18/18 dimethicone, and combinations thereof.

12. The composition of claim 1, wherein oil phase further includes dimethicone at a concentration by weight of from about 2% to about 20%, based upon weight of the composition.

13. The composition of claim 1, wherein the ratio of the aqueous phase to the oil phase is from about 4.0 to about 10.0.

14. A composition comprising:
 an aqueous phase including at least one electrolytic jasmonic acid derivative chosen from sodium tetrahydrojasmonate at a concentration by weight of from about 4% to about 10%, based upon weight of the composition, wherein the aqueous phase is at a concentration by weight of from about 80% to about 90%, based upon weight of the composition; and
 an oil phase including:
  dimethicone at a concentration by weight of from about 4% to about 15%, based upon weight of the composition; and an emulsifying crosslinked siloxane elastomer at a concentration by weight of from about 0.5% to about 7%, based upon weight of the composition; wherein the composition converts from an emulsion to a plurality of droplets upon application of shear.

15. A process for reducing signs of aging on a keratinous substrate comprising the steps of:
 (1) applying the composition of claim 1 onto the keratinous substrate; and
 (2) applying shear onto the composition, thereby transforming the composition into a plurality of droplets containing at least one electrolytic jasmonic acid derivative that is forced into the keratinous substrate.

16. The composition of claim 1 wherein the at least one electrolytic jasmonic acid derivative is present at a concentration by weight of from about 4% to about 15%, based upon weight of the composition.

17. The composition of claim 1 wherein the at least one electrolytic jasmonic acid derivative is present at a concentration by weight of from about 4% to about 10%, based upon weight of the composition.

18. The composition of claim 1 wherein the emulsifying crosslinked siloxane elastomer is present at a concentration, by weight, of about 0.3% to about 10%, based upon weight of the composition.

19. The composition of claim 1 wherein the emulsifying crosslinked siloxane elastomer is present at a concentration, by weight, of about 0.5% to about 7%, based upon weight of the composition.

* * * * *